Jan. 8, 1974 W. A. WARRINER Plant Pat. 3,423
ROSE PLANT
Filed Dec. 27, 1971
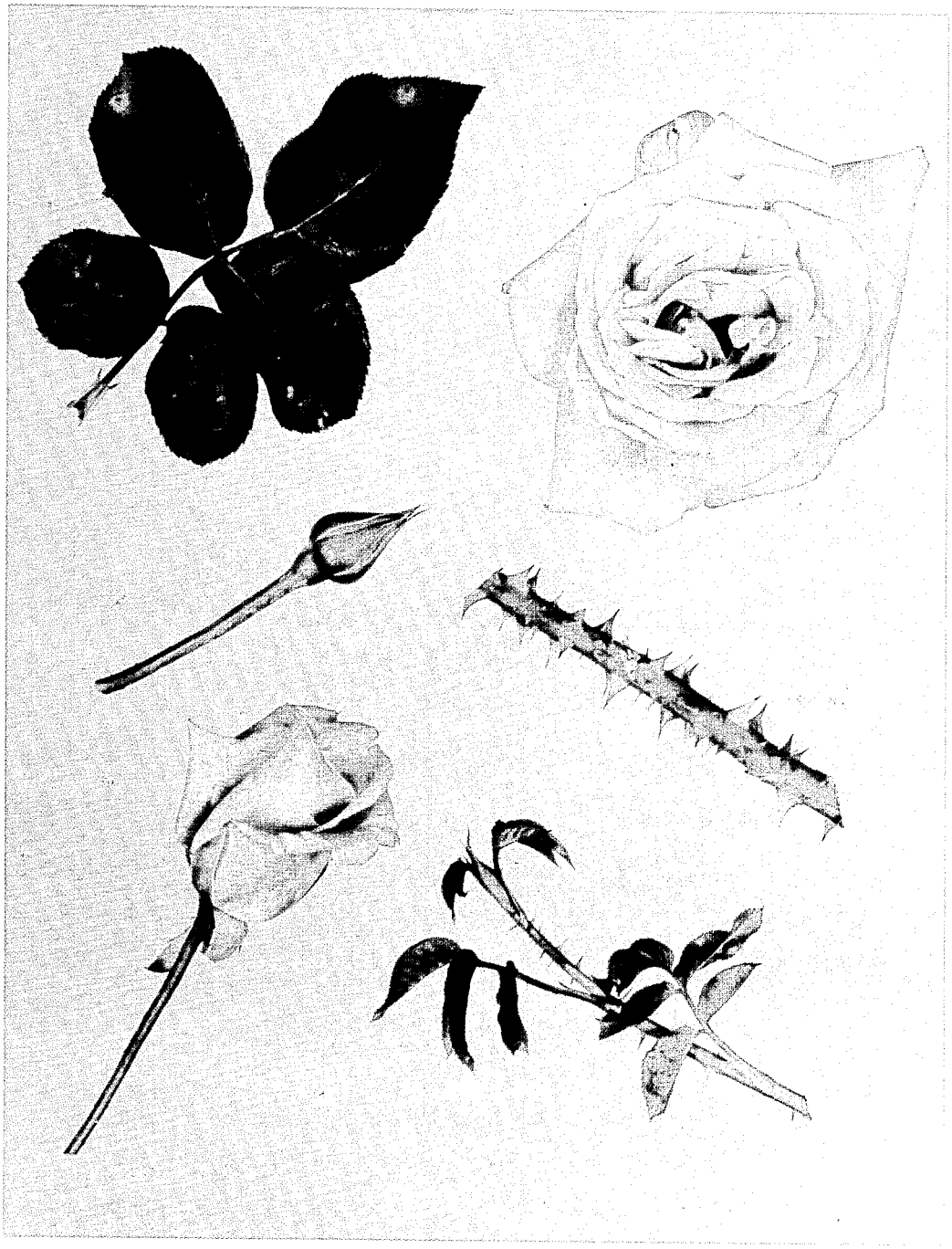
WILLIAM A. WARRINER
INVENTOR
BUCKHORN, BLORE, KLARQUST & SPARKMAN
ATTORNEYS

United States Patent Office

Plant Pat. 3,423
Patented Jan. 8, 1974

3,423
ROSE PLANT

William A. Warriner, Tustin, Calif., assignor to Jackson & Perkins Company, Medford, Oreg.

Filed Dec. 27, 1971, Ser. No. 212,839
Int. Cl. A01h 5/00
U.S. Cl. Plt.—18 1 Claim The present invention relates to a new and distinct variety of rose plant of the hybrid tea class originated by me by crossing the variety Chrysler Imperial, U.S. Plant Pat. 1,167 by the variety Virgo, unpatented.

The primary objective of this breeding was to produce a new and improved variety of the hybrid tea class of a plant habit and vigor similar to the seed parent (Chrysler Imperial) but bearing flowers of a pink color.

This objective was fully achieved along with other desirable and distinct improvements as evidence by the following unique combination of characteristics which are outstanding in the new variety and which distinguish it from its parents as well as from all other varieties of which I am aware:

(1) A vigorous, upright and well branched habit of growth.
(2) Stems growing mostly in an upright manner.
(3) Abundant, large foliage, much lighter green than either parent.
(4) Buds of Indian Lake changing quickly on opening to Phlox Pink and fading only slightly after three days open.
(5) A very strong true rose fragrance.

Asexual reproduction of my new variety by budding as performed at Wasco, Calif., shows that the aforementioned characteristics come true to form and are established and transmitted through succeeding propagations.

The accompanying drawing shows typical specimens of the vegetative growth and flowers of my new variety in different stages of development, depicted in color as nearly true as it is reasonably possible to make the same in a color illustration of this character.

The following is a detailed description of my new variety with color terminology in accordance with Wilson's "Horticultural Color Chart," except where ordinary dictionary significance of color is indicated.

Parentage: Seedling
*Seed parent.*—Chrysler Imperial.
*Pollen parent.*—Virgo.
Classification:
*Botanic.*—Rose hybrid.
*Commercial.*—Hybrid tea.

FLOWER (Observations were made in early afternoon in September at Irvine, Calif.)

Blooming habit: Recurrent—continuous.
Bud:
*Size.*—1¼" to 1½" when petals start to unfurl.
*Form.*—Long, pointed.
*Color.*—When sepals first divide—slightly lighter than Indian Lake (826/3) with darker streaks close to (826). When half blown—inside of petals—blend of Phlox Pink (625/2) and Tyrian Rose (24/1), with veins of Tyrian Rose (24); reverse of petals Phlox Pink (625)—color on reverse of petals is more uniform, veins not as prominent in color.
*Sepals.*—Color: Outer surface: Scheele's Green (860/3). Inner surface: Heavily tomentose. Three appendaged sepals lightly appendaged. Two unappendaged sepals smooth edged.

*Receptacle.*—Color: Scheele's Green (860/3). Shape: Funnel. Size: Large. Surface: Smooth.
*Peduncle.* — Length: Medium. Surface: Prickly. Color: Light green, Pod Green (061/1). Strength: Stiff, erect.
*Opening.*—Outer petals roll back slowly, giving a spiral effect.
Bloom:
*Size.*—Large. Average size when fully expanded 4".
*Borne.*—Singly and several together.
*Stems.*—Long.
*Form.*—When first open—high center. Permanence—outer petal edges slightly curled.
*Petalage.*—Thirty petals under normal conditions.
*Color.*—Center of flower: Upper side of petals—between Phlox Pink (625/1) and Phlox Pink (625/2). Reverse side of petals—Phlox Pink (625/3). Outer petals: Upper side of petals—same as inner petals. Reverse of petals—same as inner petals. Base of petals—Primrose Yellow (601/2). General tonality from a distance—Phlox Pink (625/1). No variegations.
*Discoloration.*—Third day: Slightly faded to Phlox Pink (625/3).
*Fragrance.*—Strong.
Petals:
*Texture.*—Thick.
*Surface.*—Inside—satiny. Reverse—satiny.
*Shape.*—Round.
*Form.*—Edges slightly quilled.
*Arrangement.*—Loosely imbricated.
*Petaloids in center.*—4–5 large.
*Persistence.*—Drop off cleanly.
*Lastingness.*—On the plant—long. As cut flower—long.
Reproductive parts:
*Stamens, anthers.*—Large, few; regularly arranged around styles. Color—yellow.
*Stamens, filaments (threads).*—Long. Color—reddish brown.
*Pollen.*—Color—lemon yellow.
*Styles.*—Loosely separated, of even lengths.
*Stigmas.*—Color—white.
*Ovaries.*—All enclosed in calyx.

PLANT

Form: Bush.
Growth: Very vigorous; upright; branching.
Foliage: Number of leaflets on normal mid-stem leaves—5.
*Size.*—Large.
*Quantity.*—Abundant.
*Color.*—New foliage: Near Garnet Brown (00918/3). Old foliage: Upper side: Spinach Green (0960/1). Lower side: lighter than (0960/3).
*Leaflets.*—Shape: Broadly oval. Texture: Upper side—leathery. Under side—smooth. Ribs and veins—ordinary. Edge: Serrated. Serration: Single; small. Petiole: Rachis: Color—green. Underside—prickles. Color—Pod Green (061/1). Stipules: Medium. Disease resistance: Resistant to mildew under normal growing conditions at Irvine, Calif.
Wood:
*New wood.*—Color—Light green. Bark—smooth.
*Old wood.*—Color—green. Bark—smooth.
Thorns:
*Quantity.*—On main stalks from base—many. On laterals from stalk—many.
*Form.*—Narrow base; long; hooked downward, slightly.

*Color when young.*—Green
*Position.*—Irregular.
*Prickles.*—Quantity: On main stalks—few; on laterals—few. Color: Green.
*Short needles.*—Quantity: On main stalks—none; on laterals—none.

I claim:

1. A new and distinct variety of rose plant of the hybrid tea class, substantially as herein shown and described, characterized particularly as to novelty by the unique combination of a plant branching freely from its base, bearing very freely flowers which change from Indian Lake in the tight bud to Phlox Pink in the open flower; generally light green foliage; thorny stems; long pointed flower buds; extremely strong pleasant fragrance.

No references cited.

ROBERT E. BAGWILL, Primary Examiner